(12) United States Patent
Eckstein et al.

(10) Patent No.: US 8,888,748 B2
(45) Date of Patent: Nov. 18, 2014

(54) TUBE-FIXING PLASTER

(75) Inventors: Axel Eckstein, Heidenheim (DE); Regina Merkle, Neresheim (DE); Bernd Becht, Oldendorf (DE)

(73) Assignee: Paul Hartmann AG, Heidenheim (DE)

( * ) Notice: Subject to any disclaimer, the term of this patent is extended or adjusted under 35 U.S.C. 154(b) by 904 days.

(21) Appl. No.: 12/733,124

(22) PCT Filed: Jul. 24, 2008

(86) PCT No.: PCT/EP2008/006061
§ 371 (c)(1),
(2), (4) Date: Feb. 12, 2010

(87) PCT Pub. No.: WO2009/024240
PCT Pub. Date: Feb. 26, 2009

(65) Prior Publication Data
US 2010/0163052 A1 Jul. 1, 2010

(30) Foreign Application Priority Data
Aug. 17, 2007 (DE) .......... 10 2007 038 993

(51) Int. Cl.
*A61M 5/32* (2006.01)
*A61M 16/00* (2006.01)
*A61M 25/02* (2006.01)

(52) U.S. Cl.
CPC ....... *A61M 25/02* (2013.01); *A61M 2025/0253* (2013.01); *A61M 2025/0273* (2013.01)
USPC .................. 604/180; 128/207.14

(58) Field of Classification Search
USPC .................................... 128/207.14
See application file for complete search history.

(56) References Cited

U.S. PATENT DOCUMENTS

| | | | | |
|---|---|---|---|---|
| 5,743,885 A | * | 4/1998 | Hoerby ................. 604/180 |
| 5,840,052 A | * | 11/1998 | Johns .................. 602/54 |
| 6,855,221 B1 | * | 2/2005 | Lepsius et al. ......... 156/71 |
| 2001/0001110 A1 | * | 5/2001 | Bodenschatz et al. .... 602/41 |
| 2001/0009828 A1 | * | 7/2001 | Himmelsbach et al. ... 442/35 |
| 2001/0018567 A1 | * | 8/2001 | Bodenschatz et al. .... 602/54 |
| 2004/0249328 A1 | | 12/2004 | Linnane |

FOREIGN PATENT DOCUMENTS

| | | |
|---|---|---|
| DE | 91 06 513 | 2/1992 |
| DE | 41 17 282 | 12/1992 |
| DE | 196 02 467 | 8/1996 |
| DE | 102 12 392 | 10/2003 |
| DE | 602 10 454 | 12/2006 |
| EP | 0 168 174 | 1/1986 |
| EP | 0 505 804 | 9/1992 |
| EP | 1 350 535 | 10/2003 |
| WO | WO 95/18645 | 7/1995 |
| WO | WO 99/36117 | 7/1999 |
| WO | WO 9936117 A1 * | 7/1999 |

* cited by examiner

*Primary Examiner* — Jason Flick
(74) *Attorney, Agent, or Firm* — Paul Vincent

(57) ABSTRACT

A fixing plaster (10) for fixing tubes, hoses or catheters, in particular a tube-fixing plaster (10) for fixing endotracheal tubes in particularly user-friendly form.

7 Claims, 1 Drawing Sheet

TUBE-FIXING PLASTER

This application is the national stage of PCT/EP2008/006061 filed on Jul. 24, 2008 and claims Paris Convention Priority to DE 10 2007 038 993.2 filed Aug. 17, 2007.

BACKGROUND OF THE INVENTION

The present invention concerns a fixing plaster for fixing tubes, hoses or catheters, in particular, a tube-fixing plaster for fixing endotracheal tubes in a particularly user-friendly form.

Fixing plasters have been known for a long time in emergency medicine or for operations. These fixing plasters are used, in particular, as tube-fixing plasters e.g. for endotracheal intubation of a tube into the trachea of a patient during a surgical intervention in a patient. This tube may comprise one or more hoses that are introduced into the trachea of the patient via his/her mouth, wherein the tube ensures respiration and/or anesthesia during the operation. In this connection, it is essential for the tube to be stationarily fixed during the entire surgical intervention to prevent it from getting out of place.

Fixing plasters of this type are disclosed in patent literature. The document DE 3924599 A1 e.g. describes a fixing plaster for fixing endotracheal tubes. The fixing plaster consists of an adhesive plaster having four sections, each of which is suitable to be separately fixed to the skin or to the tube or hose. DE 8500022 U1 moreover describes a holder for endotracheal tubes, which consists of an adhesive plaster, wherein fixation is realized via separate fixing strips centrally with respect to the holder. DE 20302211 U1 moreover discloses a tube-fixing plaster for oral endotracheal tubes having a base plate and four fixing reins that are connected to the base plate.

It is the underlying purpose of the present invention to provide an alternative fixing plaster, which offers a great deal of operational safety during use and also ensures high flexibility and great wear comfort during application, at the same time being inexpensive to produce.

SUMMARY OF THE INVENTION

This object is achieved by a fixing plaster in accordance with the independent claim. In accordance therewith, an inventive fixing plaster consists of a multi-layer carrier material comprising a first carrier layer, at least one second carrier layer and an adhesive layer for fixing to the skin of a patient, and has a water vapor permeability (MVTR) of at least 300 g/m²/24 h, wherein the fixing plaster consists of a base element and two fixing strips that are connected to the base element, and has a side length ratio between length and width of 5:1 to 10:1. The fixing plaster has, in particular, a side length ratio between length and width of 6:1 to 9:1 and with particular preference of 7:1 to 9:1.

In accordance with the present invention, this fixing plaster has fixing strips, each having at least one free end and one end that is connected to the base element and merges into the base element. These fixing strips therefore do not form separate elements that differ from the fixing plaster and do not form elements that might become detached from the base element. Rather, the fixing strips form, together with the base element, a unit that cannot be separated into parts.

This fixing plaster offers considerable advantages compared to conventional fixing plasters. The use of a multi-layer carrier material provides a fixing plaster having increased wear comfort, at the same time ensuring the required operational safety. The defined side length ratio and the connection between the fixing strips and the base element also provide a fixing plaster that ensures highly reliable fixation. The defined water vapor permeability provides a fixing plaster having good breathing properties. Most conventional plasters are occlusive and are consequently impermeable to water vapor and air. The defined water vapor permeability therefore provides a skin-friendly and reliable fixing plaster which adheres particularly well to the skin of a patient.

In a second preferred embodiment of the invention, the fixing strips are disposed parallel with respect to each other. It is thereby particularly advantageous for the two fixing strips to have the same length. In this connection or irrespective thereof, the fixing plaster has fixing strips which substantially have the same length as the base element. The length of the fixing strips differs, in particular, by maximally 15%, in particular maximally 10%, from the length of the base element (relative to the length of the base element).

By dividing the inventive fixing plaster into a base element and only two fixing strips having, in particular, the given proportions, the user obtains a fixing plaster that enables extremely flexible use. For fixing an endotracheal tube e.g., the base element of the fixing plaster is fixed to the right-hand or left-hand side of the mouth, i.e. laterally of the corner of the mouth, by means of the adhesive layer, wherein the side can be freely selected. The fixing plaster can then be further fixed with the first fixing strip above or below the upper or lower lip. The second fixing strip reliably fixes the tube to the corner of the mouth of the patient, wherein this fixing strip is wound at least once around the intubated tube and the free end of the strip can be fixed to the base element or the first fixing strip. Fixation to the corner of the mouth is more reliable compared to fixation in the center of the mouth, since access to the oral cavity remains free. If necessary, additional fixation in the same fashion can be realized by means of a second inventive plaster, wherein the base element of the second fixing plaster is applied on the same side of the mouth. The longitudinal axes of the base elements of the first and second fixing plasters may thereby assume an angle with respect to each other of more than 5°. These base elements and the fixing strips are then not parallel, and for this reason, the anatomy of a patient can be better taken into consideration during application. The fixing strips are thereby used in a mirror-inverted fashion, i.e. the first fixing strip of the second fixing plaster is fixed below the lower lip when the first fixing strip of the first fixing plaster is fixed above the upper lip. The second fixing strip then additionally fixes the tube by winding it once or several times and fixing it to the base element or the first fixing strip. In this fashion, the two first fixing strips can be fixed above or below the upper and lower lips, wherein the two second fixing strips that are disposed between the first fixing strips surround the tube. This obtains very reliably fixation of the tube to the corner of the mouth of the patient.

In accordance with a further preferred embodiment of the fixing plaster, the fixing plaster has a length of at least 150 mm and maximally 250 mm and, in particular, at least 170 mm and maximally 230 mm. This provides a fixing plaster that ensures reliable fixation of tubes, catheters or hoses to the skin of a patient. The longitudinal extension of the base element and the fixing strips can moreover be adjusted to a ratio that ensures fixation to the skin and also winding of the fixing strip around the tube. In connection with or irrespective of the longitudinal extension, in accordance with another preferred embodiment of the fixing plaster, the fixing plaster may have a width of at least 20 mm and maximally 40 mm and, in particular, at least 22 mm and maximally 30 mm. The width of the first fixing strip differs, in particular, by maximally 15%, in particular maximally 10%, from the width of the second fixing strip (relative to the width of the wider fixing strip). In particular, the fixing strips substantially have the same width. This provides a fixing plaster, the fixing strips of which have a width that ensures crease-free winding around the hoses and tubes and also crease-free fixation to the skin of the patient.

Another subject matter of the present invention is therefore also a tube-fixing plaster, in particular, an endotracheal tube-fixing plaster for fixing a tube to the corner of the mouth of a patient, which consists of a multi-layer carrier material comprising a first carrier layer, at least one second carrier layer and one adhesive layer for fixation to the skin of a patient, wherein the tube-fixing plaster consists of a base element and two fixing strips that are connected to the base element, and the tube-fixing plaster has a side length ratio between length and width of 5:1 to 10:1. The tube-fixing plaster has, in particular, a side length ratio between length and width of 6:1 to 9:1 and with particular preference 7:1 to 9:1.

In accordance with a particularly preferred embodiment of the present invention, the second carrier layer consists of a non-woven material which is applied, in particular, between the first carrier layer and the adhesive layer for fixing to the skin of a patient. A hydrophobic non-woven material is preferentially used as the second carrier layer. This non-woven material is advantageous in that it is particularly skin-friendly and ensures particularly good fixation of the tube-fixing plaster. However, if hydrophilic non-woven materials are used, these materials absorb liquid. The absorption of liquid, however, is not desired in the present case, since it aggravates fixation. Moreover, preferably non-woven materials are used that consist of polyester fibers, polyethylene fibers, polypropylene fibers, polyamide fibers, viscose fibers, or mixtures thereof. A non-woven material consisting of hydrophobic polyester fibers is particularly preferred.

The first carrier layer may, in particular, be a fabric, in particular a linen weave fabric, wherein this first carrier layer and the second carrier layer are also preferably undetachably connected by means of a pressure-sensitive adhesive. Compared to the non-woven material, this fabric has a high tensile strength and, in particular, stretches less. The fabric is, in particular, a hydrophobic fabric. The fabric preferentially consists of a viscose yarn, polyester yarn, polyamide yarn, polyacryl nitrile yarn or mixtures of these yarns. With particular preference, a fabric of hydrophobic viscose yarn may be used.

The use of a multi-layer carrier material, which has a fabric as a first carrier layer and a non-woven material as a second carrier layer, therefore provides a fixing plaster that is particularly skin-friendly and moreover less stretchable and therefore particularly reliable. For this reason, in particular, a fixing plaster is also a subject matter of the invention, which consists of a multi-layer carrier material having a breaking elongation in the longitudinal extension of the fixing plaster of maximally 30%, in particular maximally 25%, and preferentially maximally 20%, wherein stretching is performed with a force of at least 30 N/cm (measured in accordance with DIN EN 1940/1941 with a width of 25 mm).

A multi-layer carrier material is thereby provided, which has a high tensile strength and is also particularly skin-friendly. A multi-layer textile carrier material of a fabric and a non-woven material of this type is advantageous compared to foils or other carrier materials in that it offers good water vapor permeability and low stretching properties.

The invention is explained in more detail below with reference to drawings. In the drawings:

DESCRIPTION OF THE PREFERRED EMBODIMENT

Figure 1:
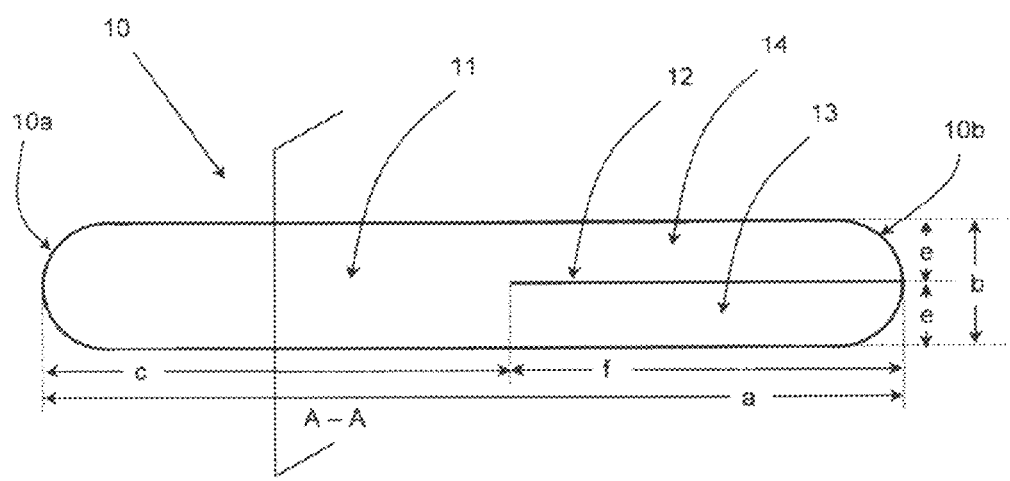
FIG. 1 shows a top view of an endotracheal tube-fixing plaster.

FIG. 1 shows a top view of an endotracheal tube-fixing plaster (10). This fixing plaster has a base element (11) and a first fixing strip (13) for fixing the plaster to the skin of a patient, and a second fixing strip (14) for fixing a tube. The base element and the fixing strips are produced from the same carrier material (20). The first fixing strip is separated from the second fixing strip through a section (12) in the carrier material (20), wherein the fixing strips are parallel to each other and have the same length.

The fixing plaster (10) has an overall length A with a=200 mm and an overall width B with b=25 mm, wherein the ends (10a, 10b) are rounded. The side length ratio between length and width of the plaster is therefore 8:1. The base element (11) has a length C with c=110 mm and a width D which corresponds to the overall width B of the fixing plaster. Each fixing strip (13, 14) has a length F with f=90 mm and a width E with e=12.5 mm.

Figure 2:
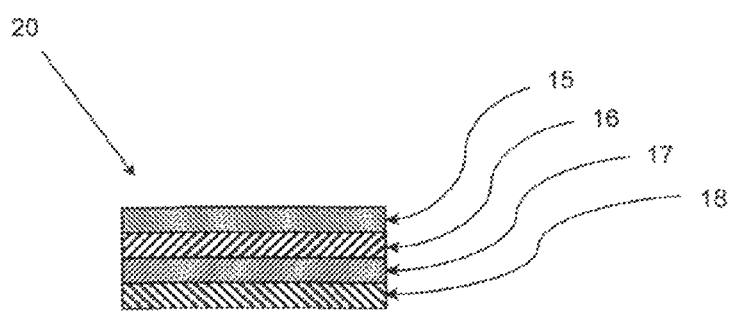
FIG. 2 shows a cross-sectional view of an endotracheal tube-fixing plaster in accordance with FIG. 1.

The fixing plaster is produced from a carrier material (20) which comprises a laminate of a first carrier layer (15) and a second carrier layer (17), wherein these two carrier layers are undetachably connected to each other, i.e. the two layers cannot be separated from each other without destroying one of the two layers (cf. FIG. 2, cross-section of the fixing plaster (10) along the sectional line A-A). These two layers are, in particular, also undetachably connected to each other during normal use. The first carrier layer (15) is produced from a non-stretchable fabric which is laminated onto the second carrier layer (17) by means of a third layer (16) which consists of a zinc oxide-containing synthetic caoutchouc (rubber) adhesive. The second carrier layer (17) is produced from a non-woven material. A transparent synthetic caoutchouc (rubber) adhesive (18) is disposed onto the non-woven material, which fixes the fixing plaster to the skin of a patient when the fixing plaster is in its normal state. This transparent adhesive is covered by a two-part release paper (not shown herein) prior to use to prevent soiling thereof.

The fabric of the first carrier layer (15) consists of 100% viscose yarn with a yarn fineness of 165 dtex (DIN 53 812 T1). The surface density is 115 g/m² (measured according to DIN 53 352). The yarn density in the warp direction is 33 yarns/cm and in the fill direction 29 yarns/cm (according to DIN 53 853). The air permeability is maximally 400 l/dm²/min measured according to DIN EN ISO 9237. The maximum tensile force elongation in the warp direction is maximally 16% and in the fill direction maximally 35% (according to DIN 53 857). This fabric is available from the company Slezan A. S., CZ-738 Frydek-Mistek (Czech Republic).

The zink oxide-containing synthetic caoutchouc (rubber) has a softening point of approximately 113° C. (measured according to DIN 52 011) and a melt viscosity of 17,700+/−3,000 mPas (measured according to Ph. Eur. 1997—method 2.2.10). The transparent synthetic caoutchouc (rubber) has a softening point of approximately 106° C. (measured according to DIN 52 011) and a melt viscosity of 15,000+/−3,000 mPas (according to Ph. Eur. 1997—method 2.2.10). Both pressure-sensitive adhesives can be obtained from the company Collano, CH-6203 Sempach-Station (Switzerland).

The non-woven material (17) is a skin-friendly needled non-woven material of polyester fibers with a surface density of approximately 45 g/m² (EDANA 40.3-90) and a density of 0.67 g/cm³ (EDANA 30.05.99). The maximum elongation of this non-woven material in the longitudinal direction is approximately 46% and in the transverse direction maximally approximately 170% according to EN 29073/3. This needled non-woven material can be obtained from the company Ahlstrom, 1-10121 Torino (Italy).

The endotracheal tube-fixing plaster (10) has a surface density of 340 g/m$^2$. The water vapor permeability (MVTR) is 383 g/m$^2$/24 h measured according to the "Deutsche Arzneibuch" (German pharmacopeia), 10. edition of 1992 (DAB 10). The adhesive force (180° peel angle) is 5.5 N/25 mm measured according to DIN EN 1939.

The endotracheal tube-fixing plaster of a width of 25 mm has a breaking elongation in the longitudinal extension of 19% and a breaking force of 30 N/cm (measured according to DIN EN 1940/1941).

This fixing plaster is particularly skin-friendly due to the use of non-woven material, and has a good water vapor permeability. The used adhesive is also insensitive to moisture, i.e. its adhesive force does not decrease through contact with perspiration or saliva. The defined values provide for a particularly user-friendly fixing plaster.

We claim:

1. An endotracheal tube fixing plaster, the plaster consisting essentially of a multi-layer carrier material having a first carrier layer and at least one second carrier layer, said first and said second carrier layers being undetachably connected to each other, and an adhesive layer for fixing to skin of a patient, wherein the plaster has a water vapor permeability (MVTR) of at least 300 g/m$^2$/24 h, said first carrier layer consisting essentially of a woven fabric and said second carrier layer consisting essentially of a non-woven material, wherein said second carrier layer is disposed between said first carrier layer and said adhesive layer for fixing to the skin of the patient, the multi-layer carrier material being structured to define a base element and two fixing strips connected to said base element, wherein said base element and said fixing strips consist of a same multilayer carrier material from which said fixing strips are formed by performing a separation cut along a length dimension of the plaster through said multilayer carrier material, thereby generating said fixing strips, said fixing strips thereby being parallel to each other and having a same length, wherein the plaster has a width of at least 20 mm and at most 40 mm and a side length ratio between length and width of 5:1 to 10:1.

2. The fixing plaster of claim 1, wherein the fixing plaster has a side length ratio between length and width of 6:1 to 9:1 or 7:1 to 9:1.

3. The fixing plaster of claim 1, wherein the fixing plaster has a width of at least 22 mm and maximally 30 mm.

4. The fixing plaster of claim 1, wherein the fixing plaster has a length of at least 150 mm and maximally 250 mm or of at least 170 mm and maximally 230 mm.

5. The fixing plaster of claim 1, wherein said first carrier layer and said second carrier layer are undetachably connected by a pressure-sensitive adhesive.

6. The fixing plaster of claim 1, wherein said fixing strips have a substantially same length as said base element.

7. Use of the fixing plaster of claim 6 as an endotracheal tube-fixing plaster.

* * * * *